（12）United States Patent
McGhie

(10) Patent No.: US 9,943,399 B2
(45) Date of Patent: Apr. 17, 2018

(54) STENT WITH POSITIONING ARMS

(71) Applicant: Cook Medical Technologies LLC, Bloomington, IN (US)

(72) Inventor: Thomas W. McGhie, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 565 days.

(21) Appl. No.: 14/160,207

(22) Filed: Jan. 21, 2014

(65) Prior Publication Data

US 2014/0207227 A1    Jul. 24, 2014

Related U.S. Application Data

(60) Provisional application No. 61/755,719, filed on Jan. 23, 2013.

(51) Int. Cl.
*A61F 2/06* (2013.01)
*A61F 2/07* (2013.01)
(Continued)

(52) U.S. Cl.
CPC .............. *A61F 2/07* (2013.01); *A61F 2/915* (2013.01); *A61F 2/954* (2013.01); *A61F 2002/075* (2013.01); *A61F 2002/821* (2013.01); *A61F 2002/91541* (2013.01); *A61F 2002/91558* (2013.01); *A61F 2002/91575* (2013.01);
(Continued)

(58) Field of Classification Search
CPC ...... A61F 2/82; A61F 2/86; A61F 2/88; A61F 2/90; A61F 2/07; A61F 2/915; A61F 2/954; A61F 2002/075; A61F 2002/821; A61F 2002/91541; A61F 2002/91558;
(Continued)

(56) References Cited

U.S. PATENT DOCUMENTS 5,397,355 A * 3/1995 Marin ..................... A61F 2/91
623/1.2
5,423,885 A    6/1995 Williams
(Continued)

FOREIGN PATENT DOCUMENTS

EP    1 044 663 A2    10/2000
JP    2005-021504    1/2005
(Continued)

OTHER PUBLICATIONS

Partial European Search Report, dated Jul. 17, 2014, pp. 1-8, European Patent Application No. 14151772.2, European Patent Office, Munich, Germany.

*Primary Examiner* — Tuan V Nguyen
(74) *Attorney, Agent, or Firm* — Brinks Gilson & Lione

(57) ABSTRACT

A stent is provided with arms for positioning the stent between two passageways. The stent may also be a stent-graft with a transition between a covered portion and an uncovered portion that is positioned relative to the junction between the two passageways. The arms are self-expanding and are biased outward from the tubular wall of the stent structure. The arms engage the wall of the first passageway around the junction to the second passageway to position a portion of the stent in the first passageway and another portion of the stent in the second passageway.

20 Claims, 5 Drawing Sheets

(51) Int. Cl.
*A61F 2/915* (2013.01)
*A61F 2/954* (2013.01)
*A61F 2/82* (2013.01)

(52) U.S. Cl.
CPC ............... *A61F 2230/0054* (2013.01); *A61F 2250/0098* (2013.01)

(58) Field of Classification Search
CPC .... A61F 2002/91575; A61F 2002/0054; A61F 2002/0098
See application file for complete search history.

(56) References Cited

U.S. PATENT DOCUMENTS

| | | | |
|---|---|---|---|
| 5,489,295 A | 2/1996 | Piplani et al. | |
| 5,562,728 A | 10/1996 | Lazarus et al. | |
| 6,334,871 B1 | 1/2002 | Dor et al. | |
| 6,451,048 B1 | 9/2002 | Berg et al. | |
| 6,503,271 B2 | 1/2003 | Duerig et al. | |
| 6,673,102 B1 | 1/2004 | Vonesh et al. | |
| 6,827,736 B2 | 12/2004 | Perouse | |
| 6,994,713 B2 | 2/2006 | Berg et al. | |
| 8,267,954 B2 | 9/2012 | Decant, Jr. et al. | |
| 2003/0220683 A1* | 11/2003 | Minasian | A61F 2/90 623/1.15 |
| 2004/0254627 A1 | 12/2004 | Thompson et al. | |
| 2010/0161027 A1 | 6/2010 | Orr | |
| 2011/0319989 A1 | 12/2011 | Lane et al. | |
| 2012/0095545 A1 | 4/2012 | Yamagata | |
| 2013/0158673 A1* | 6/2013 | Toomey | A61F 2/04 623/23.7 |
| 2013/0172983 A1* | 7/2013 | Clerc | A61F 2/848 623/1.16 |

FOREIGN PATENT DOCUMENTS

| | | |
|---|---|---|
| WO | WO 95/23563 | 9/1995 |
| WO | WO 00/15147 A1 | 3/2000 |
| WO | WO 2006/033126 A1 | 3/2006 |
| WO | WO 2008/062405 A2 | 5/2008 |

\* cited by examiner

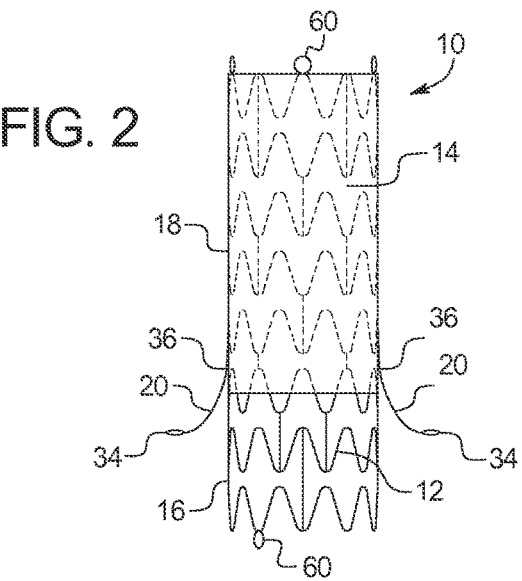
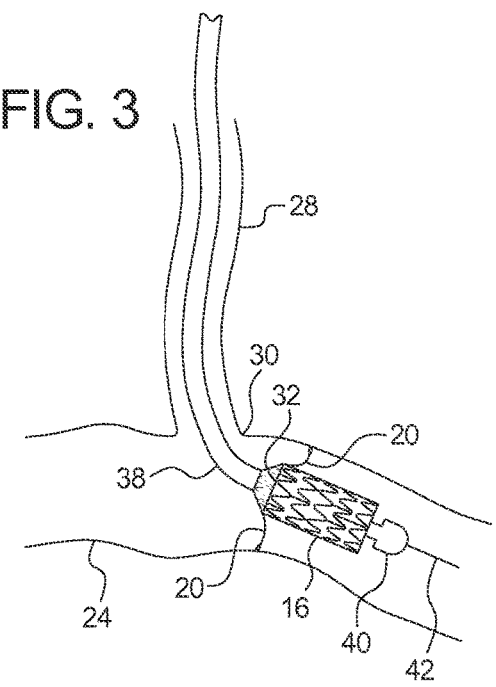
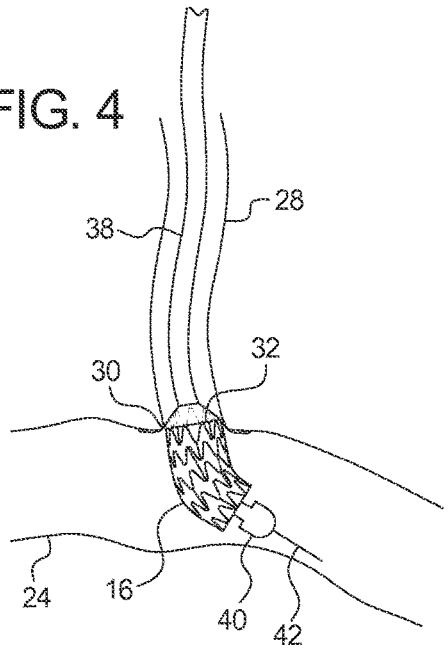

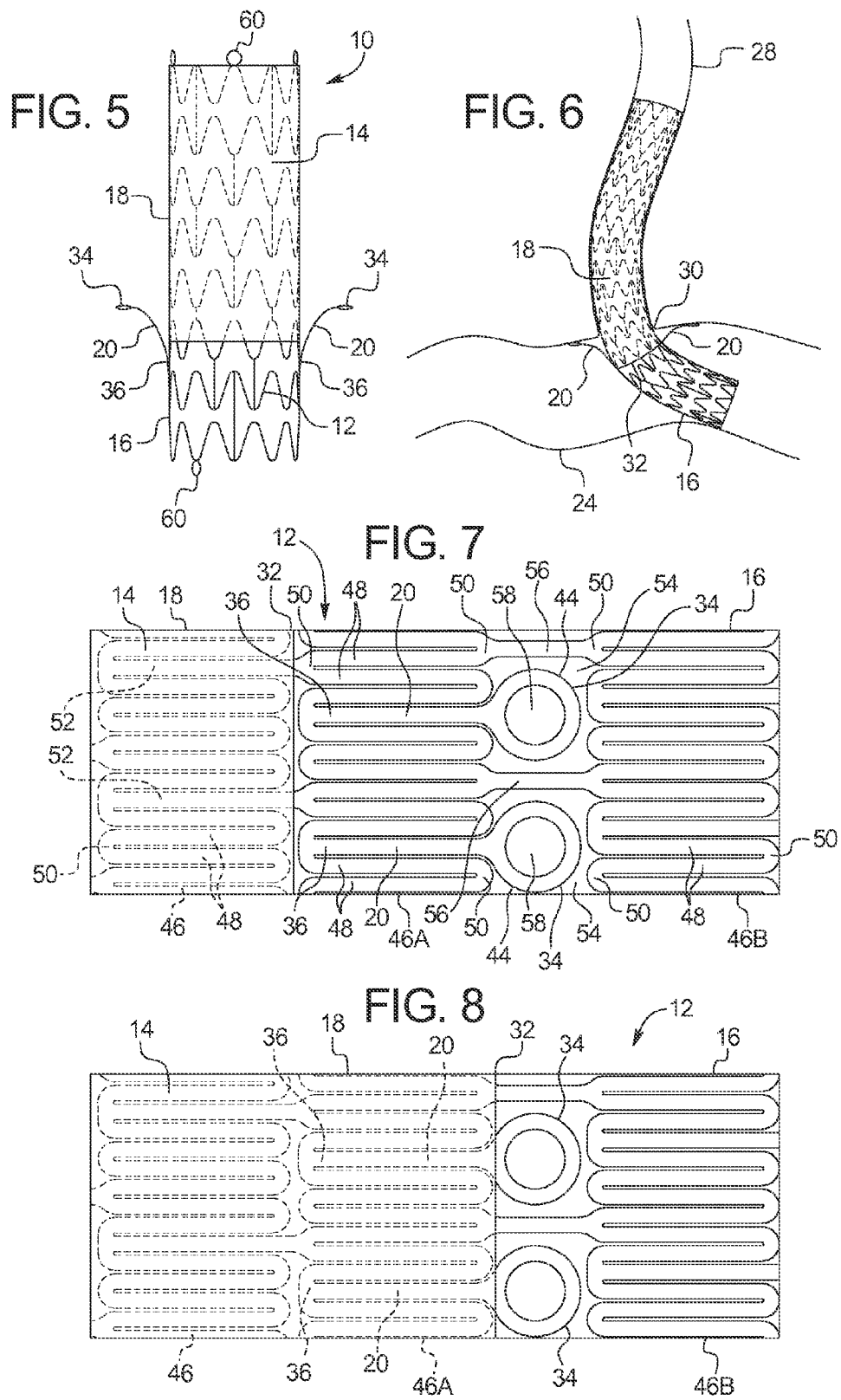

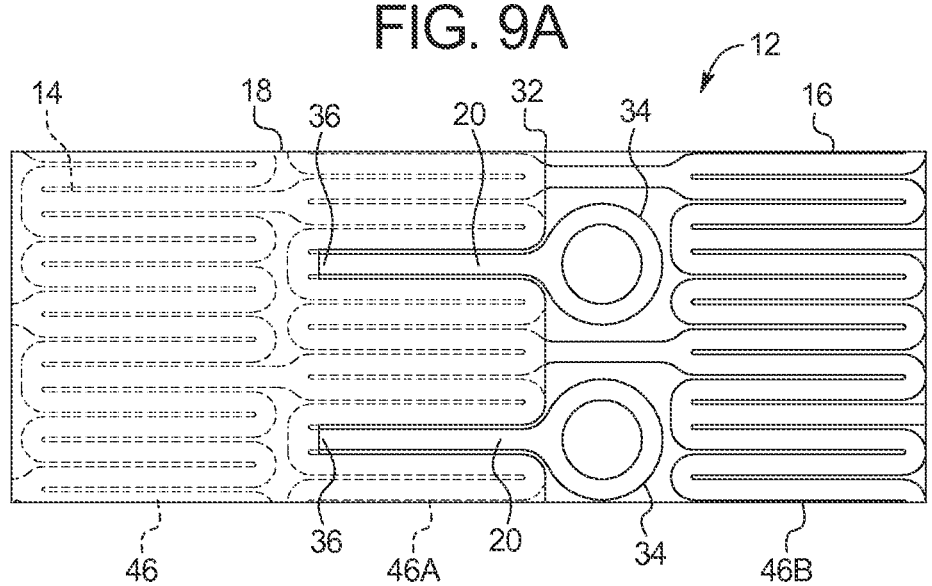
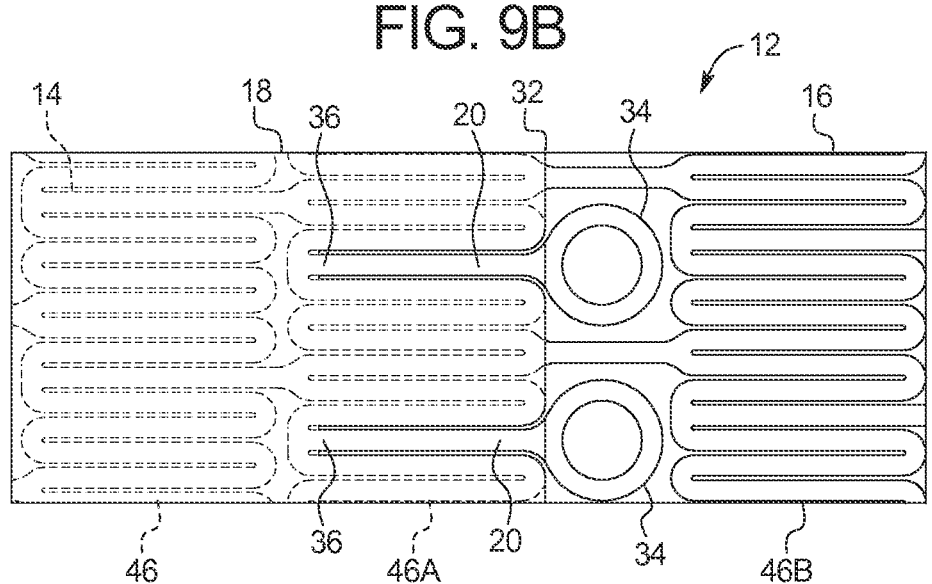

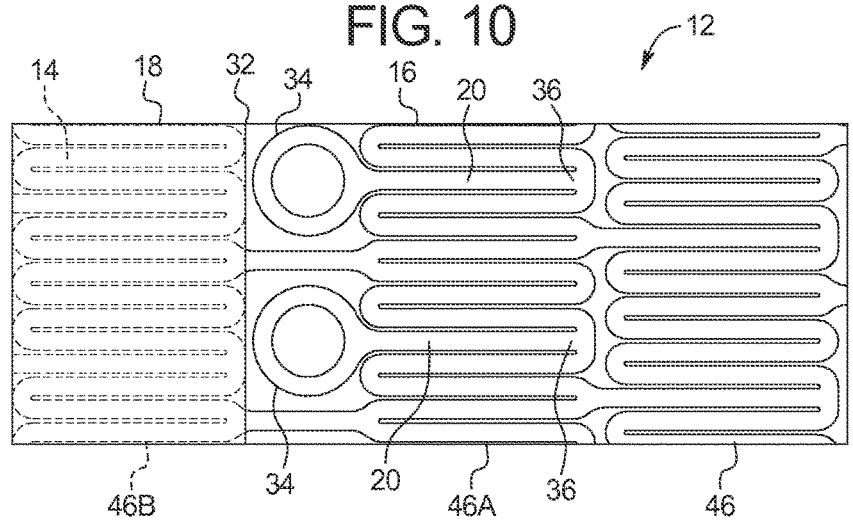
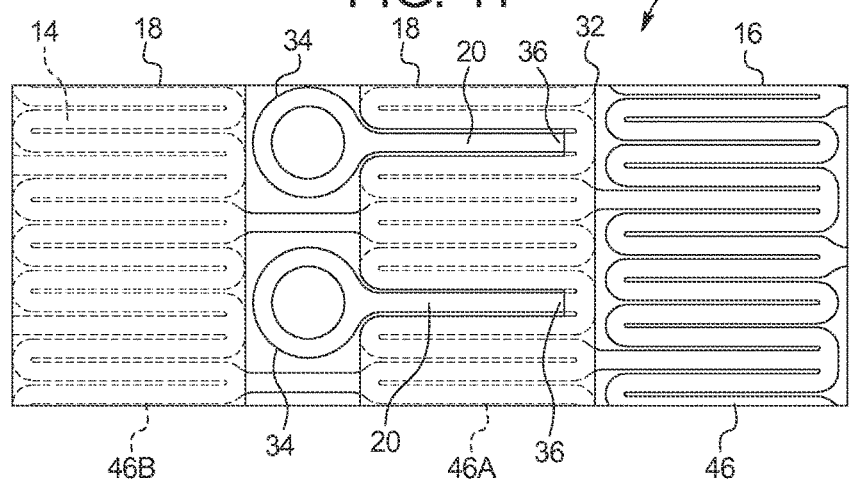
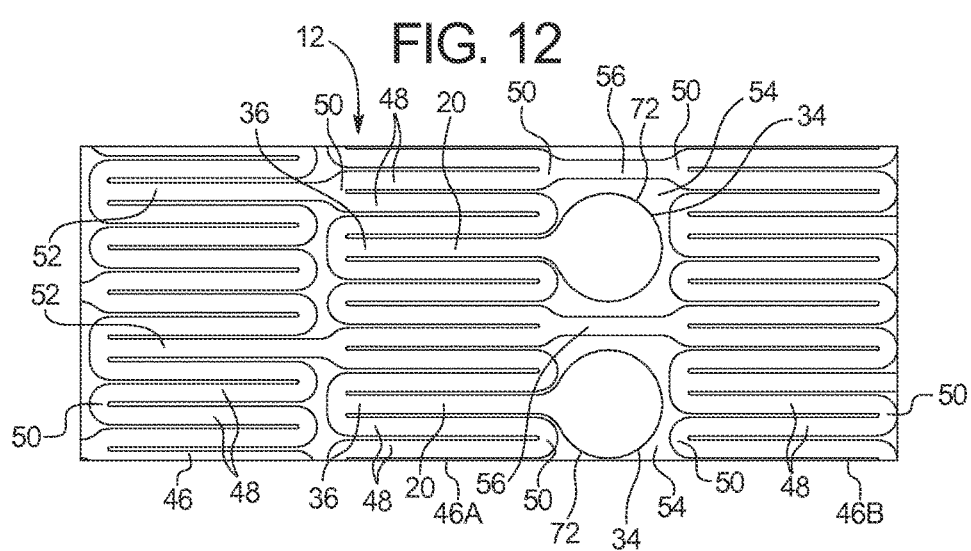

STENT WITH POSITIONING ARMS

This application claims priority to U.S. Provisional Application No. 61/755,719, filed Jan. 23, 2013, which is hereby incorporated by reference herein.

BACKGROUND

The present invention relates generally to medical devices and more particularly to a stent.

One type of intraluminal medical procedure that uses a stent-graft is the TIPS procedure. TIPS refers to a transjugular intrahepatic portalsystemic shunt that is used to treat portal hypertension that typically occurs due to chronic liver problems, such as cirrhosis. Cirrhosis of the liver may occur due to alcohol abuse or hepatitis B and C, and results in scarring of the liver tissues which reduces blood flow through the liver. Because of the reduced blood flow through the liver, blood pressure can build in the portal vein system, which can cause a number of problematic symptoms.

In order to relieve pressure in the portal vein system, a TIPS procedure involves placing a shunt in the liver between a portal vein and an hepatic vein. As a result, blood flowing through the shunt effectively bypasses the obstructed liver tissues. While this treatment does not cure the underlying liver problems that cause portal hypertension, it does diminish the side effects caused by portal hypertension and can improve a patient's quality of life and possibly extend a patient's life until a liver transplant can be performed.

In a conventional TIPS procedure, access to the patient's venous system is usually gained at the neck into the internal jugular vein. A catheter and needle are then threaded through the venous system to the inferior vena cava and an hepatic vein. From the hepatic vein, the physician penetrates through the tissues of the liver with the needle until the needle intersects a portal vein. A balloon is typically used to inflate the passageway created between the hepatic and portal veins, and a stent-graft is implanted into the passageway to maintain fluid communication between the portal vein and the hepatic vein.

Stent-grafts used in TIPS procedures typically have an uncovered portion and a covered portion that are designed, respectively, to allow blood flow through the stent wall and isolate blood flow within the lumen of the stent. For example, it is usually desirable to place the stent-graft so that a portion of the distal end of the stent-graft extends into the portal vein. This portion of the stent-graft is preferably uncovered so that blood can access the inner lumen of the stent and pass through the passageway of the shunt, but also so that blood can flow past the shunt and through the liver tissues to utilize any remaining liver function that may exist. However, the proximal portion of the stent-graft that extends through the shunt passageway is preferably covered to seal the blood flow within the lumen of the stent. This is important because the surrounding liver tissues would quickly stenos and close the shunt if a non-covered stent were used, and also because the shunt will typically intersect bile ducts between the portal and hepatic vein which would cause blood flow through the stent to quickly clot if the blood were exposed to the bile ducts.

In order to ensure that the stent-graft in a TIPS procedure performs successfully, it is important that the transition between the uncovered portion and the covered portion be accurately located at the junction between the portal vein and the shunt. For example, if the uncovered portion is positioned partially within the shunt, the opening of the shunt could stenos and obstruct blood flow into the shunt. Also, the portion of the shunt that is exposed through the uncovered portion of the stent can cause blood clotting. Conversely, if the covered portion of the stent is located within the portal vein, the covered portion can block blood flow into the lumen of the stent and past the stent-graft into the liver.

Accordingly the inventor believes it would be desirable to provide a stent with arms for positioning the stent at a junction between two passageways.

SUMMARY

A stent is described for positioning the stent relative to a junction between first and second passageways. The stent has arms that engage the wall of the first passageway at the junction so that part of the stent is located in the first passageway and part of the stent is located in the second passageway. The arms may be located adjacent a transition between an uncovered portion and a covered portion of a stent-graft. Thus, the arms may be used to position the transition between the covered and uncovered portions relative to the junction between the first and second passageways. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 2 is a side view of one embodiment of the stent-graft;

FIG. 3 is a partial cross-sectional view of the stent-graft being implanted, showing the restraining sheath withdrawn from self-expanding arms;

FIG. 4 is a partial cross-sectional view of the stent-graft being implanted, showing the stent-graft pulled into the shunt and the shunt opening compressing the arms;

FIG. 5 is a side view of another embodiment of the stent-graft;

FIG. 6 is a partial cross-sectional view of the stent-graft implanted, showing the wall of the portal vein contacting the inner surfaces of the arms;

FIG. 7 is a partial plan view of the stent-graft, showing one arrangement for the transition between the covered portion and the uncovered portion of the stent-graft;

FIG. 8 is a partial plan view of the stent-graft, showing another arrangement for the transition between the covered portion and the uncovered portion of the stent-graft;

FIG. 9A is a partial plan view of the stent-graft, showing another arrangement for the transition between the covered portion and the uncovered portion of the stent-graft;

FIG. 9B is a partial plan view of the stent-graft, showing another arrangement for the transition between the covered portion and the uncovered portion of the stent-graft.

FIG. 10 is a partial plan view of the stent-graft, showing another arrangement for the transition between the covered portion and the uncovered portion of the stent-graft;

FIG. 11 is a partial plan view of the stent-graft, showing another arrangement for the transition between the covered portion and the uncovered portion of the stent-graft; and FIG. 12 is a partial plan view of a stent without a graft covering.

DETAILED DESCRIPTION

Figure 1:
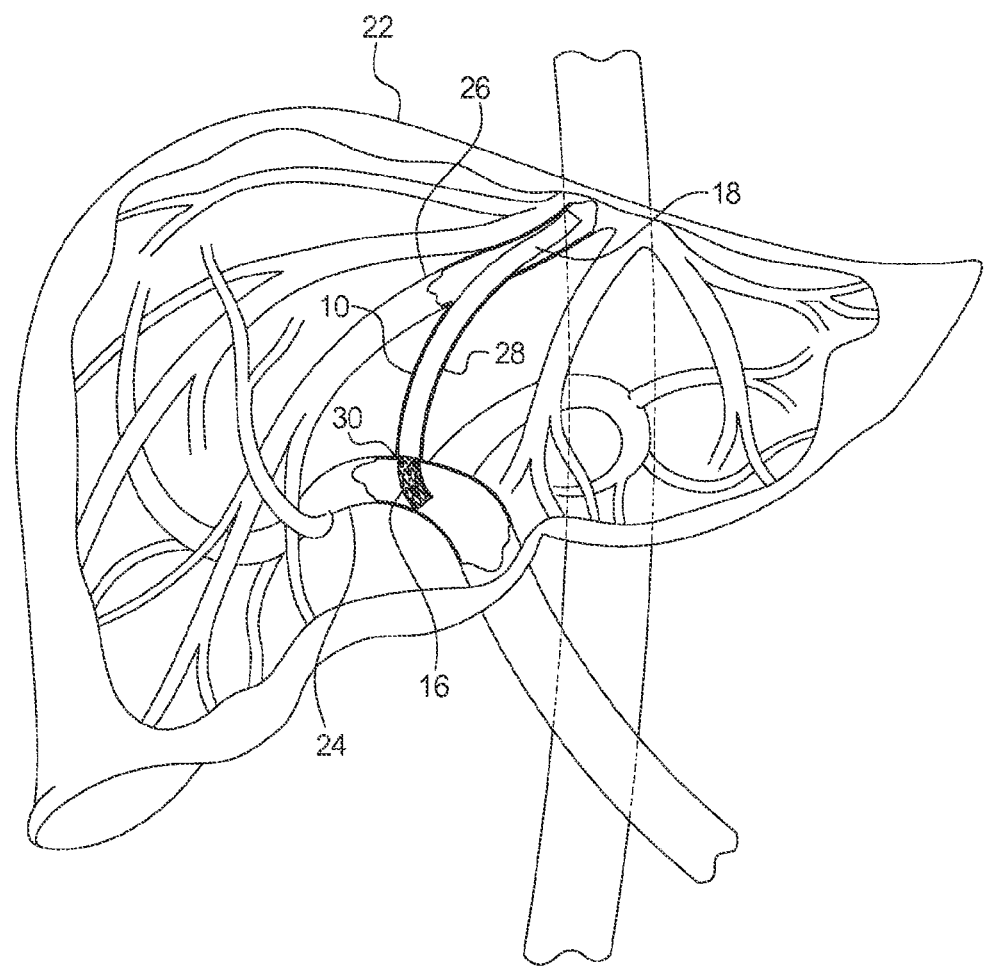
FIG. 1 is a partial cross-sectional view of a stent-graft implanted in a patient's liver.

Referring now to the figures, and particularly to FIG. 1, a stent-graft 10 is shown implanted within a patient's liver 22 following a typical TIPS procedure. As shown, the distal portion 16 of the stent-graft 10 extends into a portal vein 24, while the proximal portion 18 extends through a shunt 28 formed between the portal vein 24 and an hepatic vein 26 and within a portion of the hepatic vein 26. Preferably, the entire length of the distal portion 16 extending into the portal vein 24 is uncovered by the graft 14. On the other hand, the majority of the length of the proximal portion 18 extending from the junction 30 between the shunt 28 and the portal vein 24 is preferably covered by the graft 14. Even more preferably, the entire proximal portion 18 from the transition 32 adjacent the junction 30 between the shunt 28 and the portal vein 24 to the proximal end of the stent 12 is covered by the graft 14. The graft 14 may be made of any suitable graft material, and may be, for example, Thoralon or electrospun PTFE. It is understood that the graft 14 covering 18 may cover the outside of the stent 12, the inside of the stent 12, or the stent wall may be embedded within the covering 18. In a TIPS procedure where it is desirable to seal the liver 22 tissue surrounding the shunt 28, the graft layer 14 is preferably generally impermeable. Because the distal portion 16 is uncovered by the graft 14, blood is able to pass through the wall of the stent structure 12 to enter the lumen of the stent 12 and may also pass entirely through the stent structure 12 in order to flow through portions of liver 22 downstream from the shunt 28. By contrast, the graft 14 along the proximal portion 18 isolates the fluid passing through the lumen of the stent structure 12 to direct blood flow toward the hepatic vein 26. Thus, the shunted liver tissue is restricted from stenosing and closing the shunt and intersecting bile ducts are blocked so that blood flowing through the stent is not exposed to the bile ducts.

As shown in FIGS. 2 and 5, the stent-graft 10 may be provided with one or more arms 28 adjacent the transition 32 between the distal, uncovered portion 16 and the proximal, covered portion 18. Preferably, the stent-graft 10 has at least two arms 20, and more preferably three to five arms 20, equally spaced around the circumference of the stent structure 12. The arms 20 are preferably self-expanding so that the free end 34 of each arm 20 naturally flares outward from the wall of the stent structure 12 when there is no inward restraining force applied to the arms 20.

As shown in the embodiments of FIGS. 2-4, the free ends 34 of the arms 28 may extend toward the distal end of the stent-graft 10. Thus, the end 36 of each arm 20 that is connected to the stent structure 12 is closer to the proximal end, and the free end 34 of each arm 20 is closer to the distal end. The stent-graft 10 may be deployed as shown in FIGS. 3-4. Because the arms 20 are self-expanding, it is desirable to have an outer restraining sheath 38 that initially covers the arms 20 to press the arms 20 against the wall of the stent structure 12. As shown in FIG. 3, the arms 20 are initially located within the portal vein 24. Once the arms 20 are located in the portal vein 24, the restraining sheath 38 is withdrawn to a position proximal from the arms 20 to allow the arms 20 to expand outward from the wall of the stent structure 12. Where the stent structure 12 is also self-expanding, the distal portion 16 will self-expand as the restraining sheath 38 is withdrawn from the distal portion 16 and the arms 20. The delivery system may also be provided with an inner catheter 40 with a stop at the proximal end of the stent-graft 10 to prevent the stent-graft 10 from moving proximally with the restraining sheath 38 as the sheath 38 is withdrawn. A guidewire 42 may also pass through the lumen of the stent-graft 10 or the inner catheter 40.

As shown in FIG. 4, after the restraining sheath 38 has been partially withdrawn to allow the arms 20 to expand, the restraining sheath 38, stent-graft 10, and inner catheter 40 may be pulled together proximally into the shunt 28. When the arms 20 contact the junction 30 between the shunt 28 and the portal vein 24, the arms 28 engage the wall of the portal vein 24 at the opening 30 of the shunt 28. As the stent-graft 10 continues to move proximally, the opening 30 of the shunt 28 will begin to compress the arms 20 inward toward the wall of the stent-graft 10. As shown in FIG. 7, the free end 34 of each arm 20 is preferably provided with a radiopaque marker 44 that increases X-ray visibility of the free ends 34 of the arms 20. Thus, when the junction 30 between the shunt 28 and the portal vein 24 begins to compress the arms 20, the physician will be able to visually see the radial movement of the free ends 34 of the arms 20. As a result, this provides an indication to the physician that the transition 32 between the covered and uncovered portions 18, 16 of the stent-graft 10 is positioned adjacent the junction 30 between the shunt 28 and the portal vein 24. Once the stent-graft 10 is positioned as desired, the restraining sheath 38 may be fully withdrawn from the stent-graft 10 to implant the proximal portion 18 within the shunt 28. Because the shunt-portal vein junction 30 collapses the arms 28 toward the stent-graft 10 in the same manner that the arms 20 are collapsed prior to deployment, the arms 20 primarily provide a visual cue to the physician of the position of the covered and uncovered portions 18, 16. In other words, the arms 20 in FIGS. 2-4 provide minimal resistance to proximal movement through the opening 30 of the shunt 28. Thus, for example, in FIGS. 8 and 9, the transitions 32 between the distal and proximal portions 16, 18 can be placed close to the free ends 34 of the arms 20 so that the arms 20 are almost fully collapsed by the shunt-portal vein junction 30 when the transition 32 between the distal and proximal portions 16, 18 is positioned at the junction 30.

As shown in FIGS. 5-6, the free ends 34 of the arms 20 may alternately extend toward the proximal end of the stent-graft 10. Thus, the end 36 of each arm 20 that is connected to the stent structure 12 is closer to the distal end, and the free end 34 of each arm 20 is closer to the proximal end. The stent-graft 10 may be deployed similar to the method described above. However, in the embodiment of FIGS. 5-6, the arms 20 will provide more of a tactile cue to the position of the stent-graft 10 than the embodiment of FIGS. 2-4. That is, because the wall of the portal vein 24 engages the inside of the arms 20, the arms 20 flare further out as the arms 20 are pulled against the junction 30. Thus, the arms 20 provide significant resistance to proximal movement through the opening 30 of the shunt 28. Where the free ends 34 of the arms 28 have radiopaque markers 44, the physician may be able to see some radial outward movement of the free ends 34 of the arms 20, and a lack of proximal movement of the arms 20 in response to proximal movement of the stent-graft 10. However, tactile feedback may provide a more distinguishable indication that the arms 20 are located at the shunt opening 30.

As shown in FIG. 7, the stent structure 12 includes a series of zig-zag rings 46 made up of struts 48 connected together by bends 50. The zig-zag rings 46 may be interconnected by longitudinal connecting members 52. In FIG. 7, the stent structure 12 is shown in the collapsed configuration. As those of skill in the art will understand, when the stent structure 12 is expanded to the expanded configuration, the struts 48 will expand away from each other and will be angled with respect to the longitudinal axis of the stent 12. FIG. 7 represents only a partial view of the preferred stent 12 for a TIPS procedure, as the preferred stent 12 will be both longer and wider around the circumference. However, the full stent structure 12 can be envisioned by extending and repeating the pattern illustrated in FIG. 7. As those of skill in the art will recognize, FIG. 7 shows the stent structure 12 in a laid-out plan view, but in practice the stent structure 12 will have a tubular wall defined by the zig-zag rings 46 and an inner lumen extending lengthwise therethrough. Preferably, the entire stent structure 12 is integral, including the arms 20. Thus, the arms 20 need not be separately attached to the stent structure 12 by welding, bonding, etc. Although it is possible for the stent structure 12 to be balloon-expandable while the arms 20 are self-expanding, it is preferable for the stent structure 12 and the arms 20 to both be self-expanding.

Although the described stent-graft 10 may be used to treat a number of medical conditions, the preferred embodiment of a stent-graft 10 for a TIPS procedure will typically require a distal, uncovered portion 16 from the transition 32 to the distal end about 1 cm to about 4 cm long, and a proximal, covered portion 18 from the transition 32 to the proximal end about 3 cm to about 12 cm long. More desirably, the distal, uncovered portion 16 from the transition 32 to the distal end may be about 2 cm long, and the proximal, covered portion 18 from the transition 32 to the proximal end may be about 4 cm long. The diameter of the stent-graft 10 in the expanded diameter is also preferably about 0.6 cm to about 1.5 cm, and more preferably, about 0.8 cm to about 1.2 cm, and most preferably, about 1 cm.

As shown FIG. 7, one end 36 of each of the arms 20 may be connected to one side of one of the zig-zag rings 46A, and the free end 34 may extend to the opposing side of the zig-zag ring 46A. More preferably, the free end 34 extends past the opposing side of the zig-zag ring 46A. Unlike the other zig-zag rings 46, the adjacent zig-zag ring 46B along the opposing side may be spaced 54 farther away than the other zig-zag rings 46 to allow the free end 34 to be positioned in the extra space 54 between the rings 46A, 46B. This may be accomplished by orienting the ring 46A that the arm 20 is connected to and the adjacent ring 46B so that the outsides of two adjacent bends 50 face each other. A connector 56 about the length of the space 54 may then connect the bends 50 together. The free end 34 of the arm 20 may also have an enlarged eyelet 44 with an opening 58 through which a radiopaque material like gold or platinum can be pressed into. Thus, as noted above, the free end 34 of each of the arms 20 may have a radiopaque marker 44, which as shown in FIG. 7 may be located in the extra space 54 between the adjacent rings 46A, 46B. In order to further enhance visualization of the stent-graft 10, the distal and proximal ends of the stent structure 12 may also be provided with radiopaque markers 60 as shown in FIGS. 2 and 5.

As shown in FIGS. 7-11, the graft 14 may be positioned on the stent structure 12 in various ways depending on the characteristics of the arms 20 and the graft 14 and the desired location of the transition 32 between the covered and uncovered portions 18, 16. In FIG. 7-9 the free ends 34 of the arms 20 extend toward the distal end, while in FIGS. 10-11 the free ends 34 of the arms 20 extend toward the proximal end.

In FIG. 7, the transition 32 between the covered and uncovered portions 18, 16 may be located adjacent the end 36 of the arm 20 connected to the stent structure 12. Thus, the arm 20 and the free end 34 extending away from the connected end 36 are uncovered by the graft 14. This arrangement may be desirable where the graft 14 would be expected to exert an undesirable restraining force on the arm 20 if it was covered by the graft layer 14. Since the ring 46A that the arm 20 is attached to is uncovered, this embodiment may also be preferred where the physician is expected to stop proximal movement of the stent-graft 10 during placement when the arms 20 just begin but do not completely collapse. That is, in this arrangement, it may be preferable for only the proximal side of the uncovered ring 46A and the arm 20 to be positioned within the shunt opening 30. Alternatively, this arrangement could be used where it is acceptable for a short uncovered portion to be located in the shunt opening 30.

In FIG. 8, the transition 32 between the covered and uncovered portions 18, 16 may be located adjacent the side of the zig-zag ring 46A that is opposite from the end 36 of the arm 20 connected to the stent structure 12. Thus, the ring 46A that the arm 20 is connected to and the arm 20 itself are covered by the graft 14. However, if the free end 34 extends past the transition 32, the free end 34 may not be covered as shown in FIG. 8. This arrangement may be desirable where the graft 14 is not expected to exert an excessive restraining force on the arm 20. This arrangement may also be preferred where the physician is expected to pull the stent-graft 10 into the shunt 28 until the free ends 34 of the arms 20 are collapsed close to the wall of the stent structure 12 by the shunt opening 30. Further, this arrangement may be useful where it is desired to maximize graft 14 coverage around the shunt opening 30.

In FIGS. 9A-9B, the transition 32 between the covered and uncovered portions 18, 16 may be located adjacent the side of the zig-zag ring 46A that is opposite from the end 36 of the arm 20 connected to the stent structure 12 like FIG. 8. However, unlike FIG. 8, the arm 20 is separated from the graft 14 along the covered portion 18. For example, in FIG. 9A, this may be accomplished by masking off the arm 20 during the graft 14 coating process or by other known methods so that the arm 20 is uncovered along the covered portion 18. Alternatively, in FIG. 9B, the arm 20 may be covered by the graft 14 along the covered portion 18, but the graft 14 may be split with a razor or other cutting instrument along the sides of the arm 20. The arrangements of FIGS. 9A-9B may be desirable where the graft 14 would be expected to exert an undesirable restraining force on the arm 20 if it was covered by the graft 14 layer. Other than the separated arms 20, the arrangements of FIGS. 9A-9B could be used in a similar manner as the arrangement of FIG. 8.

In FIG. 10, the transition 32 between the covered and uncovered portions 18, 16 may be located adjacent the free end 34 of the arm 20 without covering the free end 34. This arrangement may be preferred where it is desired to have the arm 20 uncovered by the graft 14, and it is not expected that the uncovered ring 46A will substantially enter the shunt opening 30 or it is acceptable for the uncovered ring 46A to be located in the shunt opening 30.

In FIG. 11, the transition 32 between the covered and uncovered portions 18, 16 may be located adjacent the end 36 of the arm 20 connected to the stent structure 20. However, it is preferred that the free end 34 of the arm 20, and more preferably, the entire arm 20 be uncovered by the graft 14. Although it is possible that at least part of the arm 20 could be covered by the graft 14, as described above, in this arrangement the wall of the portal vein 24 at the junction 30 of the shunt 28 must be able to engage the inside surface of the free end 34 of the arm 20. Thus, a graft 14 covering that prevented the portal vein 24 wall from contacting the inside surface of the free end 34 of the arm 20 would be undesirable in the arrangements of both FIGS. 10 and 11 where the arms 20 extend toward the proximal end.

While the preferred embodiment of the device as described above is a stent-graft 12, the arms 20 may also be used with a stent 12 that is not covered by a graft 14 or a stent 12 that is fully covered by a graft 14. For example, as shown in FIG. 12, the stent 12 may have a structure as described above but without a graft 14 covering the stent 12. As shown, the arm 20 extends through the zig-zag ring 46A to which it is connected, and the free end 34 extends past the zig-zag ring 46A. Unlike the other zig-zag rings 46 that are spaced closer together, the zig-zag rings 46A, 46B at the free end 34 of the arm 20 are spaced farther apart to accommodate the portion of the free end 34 that extends past the zig-zag ring 46A. Also, the free end 34 may have an enlarged portion 72 that is wider than the width of the portion of the arm 20 that extends through the zig-zag ring 46A and the widths of the struts 48 that form the zig-zag ring 46A. Although the enlarged portion 72 is shown solid in FIG. 12, the enlarged portion 72 may also have an opening for a radiopaque marker as described above.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A stent, comprising:
   a stent structure comprising a first end, a second end, and a tubular wall extending therebetween, said tubular wall defining a lumen extending therethrough between said first and second ends, and said stent structure being expandable from a collapsed configuration to an expandable configuration, the stent structure comprising a first portion extending toward the first end and a second portion extending toward the second end; and
   an arm disposed between said first end and said second end, said arm being self-expanding outward from said tubular wall, said arm thereby being adapted to engage a wall of a first passageway to position said first portion within said first passageway and position said second portion within a second passageway, said second passageway opening into said first passageway at said wall;
   wherein said stent structure comprises a series of zig-zag rings, each zig zag ring made up of struts connected together by bends, only one zig-zag ring of the series of zig-zag rings having said arm connected at one end to one side of one of said zig-zag rings and extending through said zig-zag ring, a free end of said arm extending past an opposing side of said zig-zag ring, and an adjacent zig-zag ring along said opposing side being spaced farther from said zig-zag ring than an adjacent zig-zag ring along said one side, said free end being disposed within a space between said zig-zag ring and said adjacent zig-zag ring along said opposing side;
   wherein said one zig zag ring is connected to the adjacent zig zag ring along said one side by a longitudinal connecting member extending through the adjacent zig zag ring along said one side, and wherein said one zig zag ring is connected to the adjacent zig zag ring along said opposing side by a connector extending across said space from said opposing side of said one zig zag ring to an adjacent bend of the adjacent zig zag ring along said opposing side; and
   wherein said free end of said arm extending past said opposing side of said zig-zag ring comprises an enlarged portion with a width greater than a width of said arm extending through said zig-zag ring and a width of each strut forming said zig-zag ring.

2. A stent according to claim 1, further comprising a graft wherein
   the first portion is uncovered by the graft, and the second portion is covered by said graft, said first portion thereby being adapted to allow a fluid to pass through said tubular wall, and said second portion thereby being adapted to isolate said fluid passing through said lumen of said stent structure, said graft substantially preventing fluid flow through said tubular wall along said second portion; and
   the arm disposed adjacent a transition between said first and second portions.

3. A stent according to claim 2, wherein said first end is a distal end and said first portion is a distal portion extending from said transition to said distal end, and said second end is a proximal end and said second portion is a proximal portion extending from said transition along a length between said transition and said proximal end.

4. A stent according to claim 2, wherein the free end of said arm extends toward said first end, and said first and second portions extend from adjacent said opposing side of said zig-zag ring, said graft covering said arm along said second portion.

5. A stent according to claim 2, wherein the free end of said arm extends toward said first end, and said first and second portions extend from adjacent said opposing side of said zig-zag ring, said arm being separated from said graft along said second portion.

6. A stent according to claim 2, wherein the free end of said arm extends toward said second end, said first and second portions extend from adjacent the free end of said arm, said free end of said arm being separated from said graft.

7. A stent according to claim 2, wherein the free end of said arm extends toward said second end, said first and second portions extend from adjacent the one end of said arm connected to said stent structure disposed opposite from said free end, said free end of said arm being uncovered by said graft.

8. A stent according to claim 2, wherein said stent structure is self-expanding, further comprising at least two of said arm, wherein said arms are disposed diametrically opposed around said tubular wall.

9. A stent according to claim 8, wherein said each arm further comprises a radiopaque marker at said free end of said arm.

10. A stent according to claim 9, wherein said free end of said arm extends toward said distal end.

11. A stent according to claim 9, wherein said free end of said arm extends toward said proximal end.

12. A stent according to claim 1, wherein the free end of said arm extends toward said first end.

13. A stent according to claim 1, wherein the free end of said arm extends toward said second end.

14. A stent according to claim 1, further comprising a radiopaque marker at the free end of said arm.

15. A stent according to claim 1, wherein said first and second portions extend from adjacent the one end of said arm connected to said stent structure disposed opposite from said free end.

16. A stent according to claim 1, wherein said first portion extends to said first end and said second portion extends to said second end, said first portion being about 1 cm to about 4 cm long, said second portion being about 3 cm to about 12 cm long, and said expandable configuration of said stent structure being about 0.6 cm to about 1.5 cm in diameter.

17. A stent according to claim 1, wherein said arm is integrally formed with said stent structure, the arm and the stent structure defining a monolithic structure.

18. A stent according to claim 1, further comprising at least two of said arm, wherein said arms are disposed diametrically opposed around said tubular wall.

19. A stent according to claim 1, wherein said stent structure is self-expanding.

20. A stent, comprising:
- a stent structure comprising a distal end, a proximal end, and a tubular wall extending therebetween, said tubular wall defining a lumen extending therethrough between said distal and proximal ends, and said stent structure being expandable from a collapsed configuration to an expandable configuration, the stent structure comprising a first portion extending toward the distal end and a second portion extending toward the proximal end; and
- an arm disposed between said distal end and said proximal end, said arm being self-expanding outward from said tubular wall, said arm thereby being adapted to engage a wall of a first passageway to position said first portion within said first passageway and position said second portion within a second passageway, said second passageway opening into said first passageway at said wall;
- wherein said stent structure comprises a series of zig-zag rings, each zig zag ring made up of struts connected together by bends only one zig-zag ring of the series of zig-zag rings having said arm connected at one end to one side of one of said zig-zag rings and extending through said zig-zag ring, a free end of said arm extending past an opposing side of said zig-zag ring, and an adjacent zig-zag ring along said opposing side being spaced farther from said zig-zag ring than an adjacent zig-zag ring along said one side, said free end being disposed within a space between said zig-zag ring and said adjacent zig-zag ring along said opposing side;
- wherein said one zig zag ring is connected to the adjacent zig zag ring along said one side by a longitudinal connecting member extending through the adjacent zig zag ring along said one side, and wherein said one zig zag ring is connected to the adjacent zig zag ring along said opposing side by a connector extending across said space from said opposing side of said one zig zag ring to an adjacent bend of the adjacent zig zag ring along said opposing side; and
- wherein said free end of said arm extending past said opposing side of said zig-zag ring comprises an enlarged portion with a width greater than a width of said arm extending through said zig-zag ring and a width of each strut forming said zig-zag ring.

* * * * *